US012648721B2

(12) United States Patent
Khurana et al.

(10) Patent No.: US 12,648,721 B2
(45) Date of Patent: Jun. 9, 2026

(54) APPARATUS AND METHOD FOR DETERMINING OXYGEN SATURATION WITH SKIN TONE CORRECTION

(71) Applicants: Vikas Khurana, South Abington Township, PA (US); Hugh S. Fairman, Stillwater, NJ (US)

(72) Inventors: Vikas Khurana, South Abington Township, PA (US); Hugh S. Fairman, Stillwater, NJ (US)

( * ) Notice: Subject to any disclaimer, the term of this patent is extended or adjusted under 35 U.S.C. 154(b) by 0 days.

(21) Appl. No.: 19/044,536

(22) Filed: Feb. 3, 2025

(65) Prior Publication Data

US 2025/0248629 A1 Aug. 7, 2025

Related U.S. Application Data

(60) Provisional application No. 63/549,457, filed on Feb. 3, 2024.

(51) Int. Cl.
*A61B 5/1455* (2006.01)
*A61B 5/00* (2006.01)

(52) U.S. Cl.
CPC ........ *A61B 5/14552* (2013.01); *A61B 5/7271* (2013.01)

(58) Field of Classification Search
CPC .............. A61B 5/1455; A61B 5/14551; A61B 5/14552; A61B 5/7203; A61B 5/7225; A61B 5/7271
See application file for complete search history.

(56) References Cited

U.S. PATENT DOCUMENTS

| | | | | |
|---|---|---|---|---|
| 7,532,919 | B2 * | 5/2009 | Soyemi | A61B 5/14551 600/323 |
| 10,820,863 | B2 * | 11/2020 | Bechtel | A61B 5/14552 |
| 2023/0043376 | A1 * | 2/2023 | Maderic | A61B 5/14552 |

* cited by examiner

*Primary Examiner* — Eric F Winakur
(74) *Attorney, Agent, or Firm* — Nitin Kaushik

(57) ABSTRACT

Disclosed is an apparatus (100) for determining oxygen saturation with skin tone correction. The apparatus includes first (102) and second (104) probes adapted to be disposed on a body portion (106) having first through third absorbers, and configured to emit and detect light signals corresponding to a set of wavelengths. The apparatus further includes processing circuitry (116) coupled to the probes and configured to: determine reflectance and transmittance values based on the detected light signals; determine and rescale first and second sets of absorbance values corresponding to the reflectance and transmittance values; determine first through third coefficients of the first through third absorbers; and determine an oxygen saturation value based on the first and second coefficients such that the oxygen saturation value is corrected for skin and tissue absorption.

16 Claims, 6 Drawing Sheets

100

104

106

102

400

402 — Emit and detect light signals using first and second probes

404 — Determine reflectance and transmittance values

406 — Determine and rescale absorbance values

408 — Determine and Classify skin tone using huvic scale

410 — Adjust absorbance values based on skin tone

412 — Determine coefficients of absorbers

416 — Determine oxygen saturation value

APPARATUS AND METHOD FOR DETERMINING OXYGEN SATURATION WITH SKIN TONE CORRECTION

CROSS-REFERENCE TO RELATED APPLICATIONS

This non-provisional application claims the benefit under 35 U.S.C. § 119 (e) of U.S. Provisional patent application Ser. No. 63/549,457, entitled APPARATUS AND METHOD FOR DETERMINING TISSUE OXYGEN SATURATION WITH CORRECTION FOR SKIN AND TISSUE ABSORPTION, filed Feb. 3, 2024, the disclosure of which is incorporated by reference herein in their entirety.

FIELD OF DISCLOSURE

The present disclosure relates to medical instrumentation for monitoring oxygen saturation levels in tissues using optical means, and more particularly to an apparatus and method for determining tissue oxygen saturation with correction for skin and tissue absorption.

BACKGROUND

The present disclosure relates to medical instrumentation for monitoring oxygen saturation levels in tissue using optical means. Accurate measurement of oxygen saturation is crucial in various medical settings, particularly during surgery and in critical care situations. The ability to monitor oxygen levels in blood and tissue provides valuable information about a patient's physiological state and can guide medical interventions.

Conventional methods for measuring oxygen saturation often utilize optical techniques based on the differential absorption of light by oxygenated and deoxygenated hemoglobin. These methods typically involve emitting light at specific wavelengths into tissue and detecting the reflected or transmitted light. However, existing systems may face challenges in accurately accounting for variations in skin pigmentation and tissue composition among different individuals. Additionally, some current devices may struggle to provide reliable measurements across a wide range of skin tones, potentially leading to inaccuracies in oxygen saturation readings for certain patient populations.

Furthermore, many available oxygen saturation monitoring devices do not adequately address the impact of skin and tissue absorption on measurement accuracy. This can result in inconsistent or unreliable readings, especially in patients with darker skin tones or in situations where tissue properties may vary significantly. The inability to correct for these factors can limit the applicability and effectiveness of oxygen saturation monitoring in diverse clinical settings.

Therefore, there exists a need for a technical solution that addresses the aforementioned limitations of conventional systems and methods for determining tissue oxygen saturation.

SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

In an aspect of the present disclosure, an apparatus is disclosed. The apparatus includes first and second probes adapted to be disposed on a body portion having first through third absorbers. The first absorber is oxyhaemoglobins, the second absorber is deoxyhaemoglobins, and the third absorber is skin/tissues. The probes are configured to emit and detect a set of light signals corresponding to a set of wavelengths. The apparatus includes processing circuitry coupled to the first and second probes. The processing circuitry is configured to determine a set of reflectance values and a set of transmittance values based on the set of light signals detected by one of the first probe, the second probe, or a combination thereof. The processing circuitry is configured to determine and rescale first and second set of absorbance values corresponding to the set of reflectance values and the set of transmittance values, respectively. Each absorbance value of the first and second set of absorbance values are rescaled with respect to predefined absorbance values of the first and second absorbers. The processing circuitry is configured to determine first through third coefficients of the first through third absorbers, respectively. The processing circuitry is configured to determine an oxygen saturation value based on the first and second coefficients such that the oxygen saturation value is corrected for skin and tissue absorption.

In some aspects of the present disclosure, the processing circuitry is configured to control one of the first probe or the second probe to emit the set of light signals in an interval of 10 nm within a visible wavelength range of 400 nanometres (nm) to 700 nm.

In some aspects of the present disclosure, the first probe includes a first emitter and a first detector. The second probe includes a second emitter and a second detector. The first and second emitter are configured to emit a first and second set of light signals to illuminate a first and second side of the body portion, respectively. The first detector is configured to detect a set of reflected signals of the first set of light signals and to detect a set of transmitted signals of the second set of light signals. The second detector is configured to detect a second set of reflected signals of the second set of light signals and to detect a set of transmitted signals of the first set of light signals.

In some aspects of the present disclosure, the processing circuitry is configured to determine and rescale the first and second set of absorbance values by way of an equation: rescaled absorbance=(100−reflectance value)/0.00025.

In some aspects of the present disclosure, the processing circuitry is configured to determine the first through third coefficients of the first through third absorbers, respectively, by performing matrix multiplication of Moore-Penrose pseudoinverse of a first matrix formed that is based on the set of wavelengths, the rescaled first set of absorbance values, and the predefined absorbance values of the first and second absorbers, to a second matrix formed that is based on rescaled second set of absorbance values.

In some aspects of the present disclosure, the processing circuitry is configured to determine the oxygen saturation value by way of an equation: oxygen Saturation=(100*first coefficient)/(first coefficient+second coefficient).

In some aspects of the present disclosure, the processing circuitry is configured to determine the first and second set of absorbance values corresponding to the set of reflectance values and the set of transmittance values by way of an equation: absorbance=(100−reflectance value). The processing circuitry is configured to rescale the determined first and second set of absorbance values by way of an equation: rescaled absorbance=absorbance/0.00025.

In some aspects of the present disclosure, the processing circuitry is configured to determine and classify a skin tone of the body portion by way of a huvic scale. The processing circuitry is configured to adjust the determined first and second set of absorbance values based on the classified skin tone of the body portion.

In an aspect of the present disclosure, a method is disclosed. The method includes emitting and detecting, by way of first and second probes disposed on a body portion having first through third absorbers, a set of light signals corresponding to a set of wavelengths. The first absorber is oxyhaemoglobins, the second absorber is deoxyhaemoglobins, and the third absorber is skin/tissues. The method includes determining, by way of processing circuitry coupled to the first and second probes, a set of reflectance values and a set of transmittance values based on the set of light signals detected by one of the first probe, the second probe, or a combination thereof. The method includes determining and rescaling, by way of the processing circuitry, first and second set of absorbance values corresponding to the set of reflectance values and the set of transmittance values, respectively. Each absorbance value of the first and second set of absorbance values are rescaled with respect to predefined absorbance values of the first and second absorbers. The method includes determining, by way of the processing circuitry, first through third coefficients of the first through third absorbers, respectively. The method includes determining, by way of the processing circuitry, an oxygen saturation value based on the first and second coefficients such that the oxygen saturation value is corrected for skin and tissue absorption.

In some aspects of the present disclosure, the method includes controlling, by way of the processing circuitry, one of the first probe or the second probe, to emit the set of light signals in an interval of 10 nm within a visible wavelength range of 400 nanometres (nm) to 700 nm.

In some aspects of the present disclosure, the first probe includes a first emitter and a first detector. The second probe includes a second emitter and a second detector. The method includes emitting, by way of the first and second emitter, a first and second set of light signals to illuminate a first and second side of the body portion, respectively. The method includes detecting, by way of the first detector, a set of reflected signals of the first set of light signals and a set of transmitted signals of the second set of light signals. The method includes detecting, by way of the second detector, a second set of reflected signals of the second set of light signals and a set of transmitted signals of the first set of light signals.

In some aspects of the present disclosure, determining and rescaling the first and second set of absorbance values includes applying an equation: rescaled absorbance=(100−reflectance value)/0.00025.

In some aspects of the present disclosure, determining the first through third coefficients of the first through third absorbers, respectively, includes performing matrix multiplication of Moore-Penrose pseudoinverse of a first matrix formed that is based on the set of wavelengths, the rescaled first set of absorbance values and the predefined absorbance values of the first and second absorbers, to a second matrix formed that is based on rescaled second set of absorbance values.

In some aspects of the present disclosure, determining the oxygen saturation value includes applying an equation: oxygen Saturation=(100*first coefficient)/(first coefficient+second coefficient).

In some aspects of the present disclosure, the method includes determining the first and second set of absorbance values corresponding to the set of reflectance values and the set of transmittance values by applying an equation: absorbance=(100−reflectance value). The method includes rescaling the determined first and second set of absorbance values by applying an equation:

$$\text{rescaled absorbance}=\text{absorbance}/0.00025.$$

In some aspects of the present disclosure, the method includes determining and classifying, by way of the processing circuitry, a skin tone of the body portion using a huvic scale. The method includes adjusting the determined first and second set of absorbance values based on the classified skin tone of the body portion.

The foregoing general description of the illustrative aspects and the following detailed description thereof are merely exemplary aspects of the teachings of this disclosure and are not restrictive.

BRIEF DESCRIPTION OF FIGURES

The following detailed description of the preferred aspects of the present disclosure will be better understood when read in conjunction with the appended drawings. The present disclosure is illustrated by way of example, and not limited by the accompanying figures, in which like references indicate similar elements.

DETAILED DESCRIPTION

The present disclosure relates to an apparatus and method for determining tissue oxygen saturation with correction for skin and tissue absorption. Oxygen saturation measurement may be an valuable tool in medical diagnostics and patient monitoring. However, traditional methods of measuring oxygen saturation may be affected by variations in skin tone and tissue composition among patients. The present disclosure addresses this challenge by providing an improved approach that may account for these variations, potentially leading to more accurate oxygen saturation measurements across diverse patient populations.

The apparatus and method described herein may utilize both reflectance and transmittance measurements of light signals at multiple wavelengths. By combining these measurements with known spectral data for oxyhemoglobin and deoxyhemoglobin, the system may determine oxygen saturation levels while correcting for the effects of skin and tissue absorption.

An aspect of the present disclosure may be a feature that incorporates skin tone classification and correction of absorbance measurement. The feature may allow the system to adapt its measurements based on the specific skin characteristics of each patient, potentially improving accuracy across a wide range of skin tones.

The apparatus may include specialized probes for emitting and detecting light signals, along with processing circuitry for analyzing the detected signals and calculating oxygen saturation values. The method may involve a series of steps including light signal emission and detection, determination of reflectance and transmittance values, determination and rescaling of absorbance values, correction of rescaled absorbance values based skin tone and ultimately, the determination of oxygen saturation.

This improved approach to oxygen saturation measurement may have applications in various medical settings, from routine check-ups to critical care monitoring. By providing more accurate measurements across diverse patient populations, the present disclosure may contribute to enhanced patient care and more informed medical decision-making.

Figure 1A:
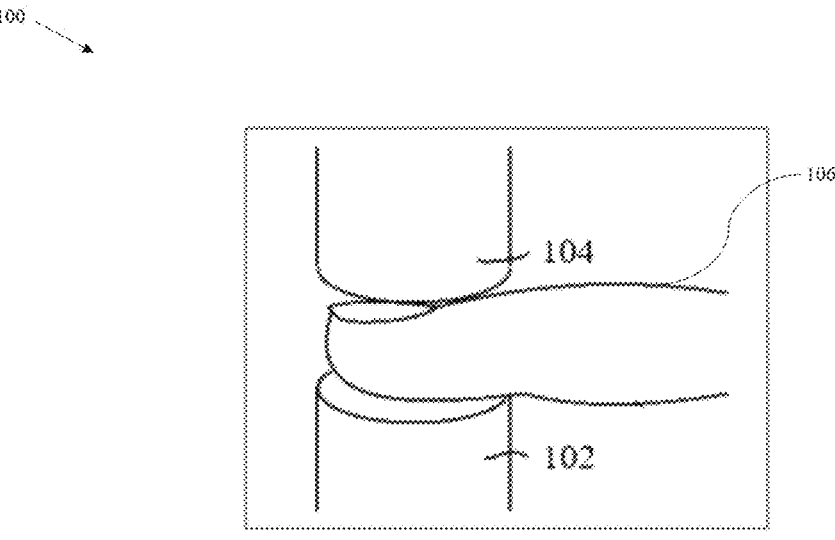
FIG. 1A illustrates a side view of an apparatus for measuring oxygen saturation, according to an aspect of the present disclosure.

FIG. 1A illustrates a side view of an apparatus 100 for measuring oxygen saturation, according to an aspect of the present disclosure. The apparatus 100 may include a first probe 102 and a second probe 104 disposed on opposite sides of a body portion 106. The first probe 102 may be positioned on one side of the body portion 106, while the second probe 104 may be positioned on the opposite side. The first probe 102 and the second probe 104 may be arranged to enable both transmission and reflectance measurements through the body portion 106. The body portion 106 may be positioned between the first probe 102 and second probe 104 in a manner that allows light signals emitted from the first probe 102 and/or the second probe 104 to pass through the tissue for measurement purposes. The arrangement of the first probe 102 and the second probe 104 may facilitate the detection of light signals that are either transmitted through or reflected from the body portion 106.

The apparatus 100 may be configured to measure oxygen saturation in the body portion 106. The first probe 102 and the second probe 104 may be adapted to be disposed on the body portion 106 having first through third absorbers. In some aspects of the present disclosure, the first absorber may be oxyhaemoglobins, the second absorber may be deoxyhaemoglobins, and the third absorber may be skin/tissues.

The first probe 102 and the second probe 104 may be configured to emit and detect a set of light signals corresponding to a set of wavelengths. The set of wavelengths may be in a visible range of light i.e., 400 nm-700 nm such that each wavelength of the set of wavelengths are 10 nm apart from each other. Aspects of the present disclosure are intended to include or otherwise cover any other wavelength range of light and any other value of interval between the wavelength range of the light, without deviating from the scope of the present disclosure.

In some aspects of the present disclosure, the first probe 102 and the second probe 104 may be adapted to be disposed on the body portion 106 in a manner that ensures consistent and reliable measurements. The probes may be designed to maintain proper contact with the skin surface while minimizing discomfort to a user. Specifically, the first probe 102 and the second probe 104 may be disposed to the body portion 106 in a manner parallel to each other or at a certain angle from each other. The arrangement of the first probe 102 and the second probe 104 may allow for accurate measurement of both reflectance and transmittance values, which may be used to determine oxygen saturation levels.

The apparatus 100 may offer several advantages. By utilizing both reflectance and transmittance measurements, the apparatus 100 may provide more accurate oxygen saturation readings compared to devices that rely on a single measurement type. Furthermore, the apparatus 100 may provide correction for skin and tissue absorption, which may enhance the precision of the oxygen saturation determination, particularly across diverse skin tones.

Examples of the first probe 102 and the second probe 104 may include, but are not limited to, optical sensors, photodiodes, phototransistors, or any other light-sensitive devices capable of detecting reflected and transmitted light signals. Aspects of the present disclosure are intended to include and/or otherwise cover any type of probe known to a person having ordinary skill in the art, without deviating from the scope of the present disclosure.

Although FIG. 1A illustrates that the apparatus 100 includes a single first probe 102 and a single second probe 104, it may be apparent to a person skilled in the art that the scope of the present disclosure may not be limited to it. In various other aspects, the apparatus 100 may include multiple first probes and multiple second probes without deviating from the scope of the present disclosure. In such a scenario, each first probe and each second probe may be configured to perform one or more operations in a manner similar to the operations of the first probe 102 and the second probe 104 as described herein.

In some aspects of the present disclosure, the body portion 106 may be a finger, preferably an index finger. However, aspects of the present disclosure are not limited to this and may include other body portions including, but not limited to an earlobe, a forehead portion or any other body portion by way of which enough light may be transmitted through blood-containing tissues to obtain an accurate oxygen saturation measurement.

Figure 1B:
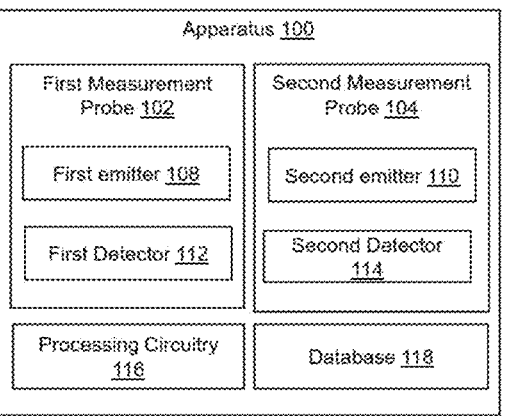
FIG. 1B illustrates a block diagram of the apparatus for measuring the oxygen saturation, according to another aspect of the present disclosure.

FIG. 1B illustrates a block diagram of the apparatus 100 for measuring the oxygen saturation, according to another aspect of the present disclosure. The apparatus 100 may include the first probe 102 and the second probe 104, a first emitter 108, a second emitter 110, a first detector 112, a second detector 114, processing circuitry 116, and a database 118.

The first probe 102 may include the first light emitter 108 and the first detector 112. The first light emitter 108 may be configured to emit a first set of light signals to illuminate a first side of the body portion 106. In some aspects of the present disclosure, the first light emitter 108 may be configured to emit light signals in an interval of 10 nm within a visible wavelength range of 400 nanometres (nm) to 700 nm. The first detector 112 may be configured, to detect a set of reflected signals of the first set of light signals and to detect a set of transmitted signals of the second set of light signals.

The second probe 104 may include the second light emitter 110 and the second detector 114. The second light emitter 110 may be configured to emit a second set of light signals to illuminate a second side of the body portion 106. In some aspects of the present disclosure, the second light emitter 110 may be configured to emit light signals in an interval of 10 nm within a visible wavelength range of 400 nanometres (nm) to 700 nm. The second detector 114 may be configured, to detect a second set of reflected signals of the second set of light signals and/or to detect a set of transmitted signals of the first set of light signals.

The first light emitter 108 and the second light emitter 110 may be configured to emit light signals at specific wavelengths to illuminate the body portion 106. The emitted light signals may interact with the absorbers within the body portion 106, resulting in reflected and transmitted light signals that are detected by the respective detectors.

Examples of the first light emitter 108 and the second light emitter 110 may include, but are not limited to, light-emitting diodes (LEDs), laser diodes, or any other light-emitting devices capable of producing light at specific wavelengths. Aspects of the present disclosure are intended to include and/or otherwise cover any type of light emitter known to a person having ordinary skill in the art, without deviating from the scope of the present disclosure.

In some aspects of the present disclosure, the set of light signals corresponding to the set of wavelengths may be produced by way of a plurality of band pass filters. Aspects of the present disclosure are intended to include or otherwise may cover any known, related, or later developed technologies to produce the set of light signals corresponding to the set of wavelengths.

Examples of the first detector 112 and the second detector 114 may include, but are not limited to, photodiodes, phototransistors, or any other light-sensitive devices capable of detecting light signals. Aspects of the present disclosure are intended to include and/or otherwise cover any type of detector known to a person having ordinary skill in the art, without deviating from the scope of the present disclosure.

The processing circuitry 116 may be coupled to the first probe 102 and the second probe 104. The processing circuitry 116 may be configured to determine a set of reflectance values and a set of transmittance values based on the set of light signals detected by one of, the first probe 102, the second probe 104, or a combination thereof.

In some aspects of the present disclosure, the processing circuitry 116 may be configured to determine and rescale first and second set of absorbance values corresponding to the set of reflectance values and the set of transmittance values, respectively. Each absorbance value of the first and second set of absorbance values may be rescaled with respect to predefined absorbance values of the first and second absorbers. The processing circuitry 116 may determine and rescale the absorbance values using an equation:

$$rescaledabsorbance = (100 - reflectancevalue)/0.00025$$

The processing circuitry 116 may be further configured to determine first through third coefficients of the first through third absorbers, respectively. In some aspects of the present disclosure, the processing circuitry 116 may determine these coefficients by performing matrix multiplication of Moore-Penrose pseudoinverse of a first matrix formed that may be based on the set of wavelengths, the rescaled first set of absorbance values, and the predefined absorbance values of the first and second absorbers, to a second matrix formed that may be based on rescaled second set of absorbance values.

In some aspects of the present disclosure, the processing circuitry 116 may be configured to determine an oxygen saturation value based on the first and second coefficients such that the oxygen saturation value may be corrected for skin and tissue absorption. The processing circuitry 116 may determine the oxygen saturation value using an equation:

$$oxygenSaturation =$$

$$(100 * firstcoefficient)/(firstcoefficient + secondcoefficient)$$

The database 118 may be coupled to the processing circuitry 116. The database 118 may be configured to store logic, instructions, circuitry, interfaces, and/or codes of the processing circuitry 116 to enable the processing circuitry 116 to execute the one or more operations associated with the apparatus 100. The database 118 may be further configured to store therein, data associated with the apparatus 100, and the like.

Examples of the database 118 may include but are not limited to, a Relational database, a NoSQL database, a Cloud database, an Object oriented database, and the like. Aspects of the present disclosure are intended to include or otherwise cover any type of the database 118 including known, related art, and/or later developed technologies. In some aspects of the present disclosure, a set of centralized or distributed network of peripheral memory devices may be interfaced with the apparatus 100, as an example, on a cloud server.

Figure 1C:
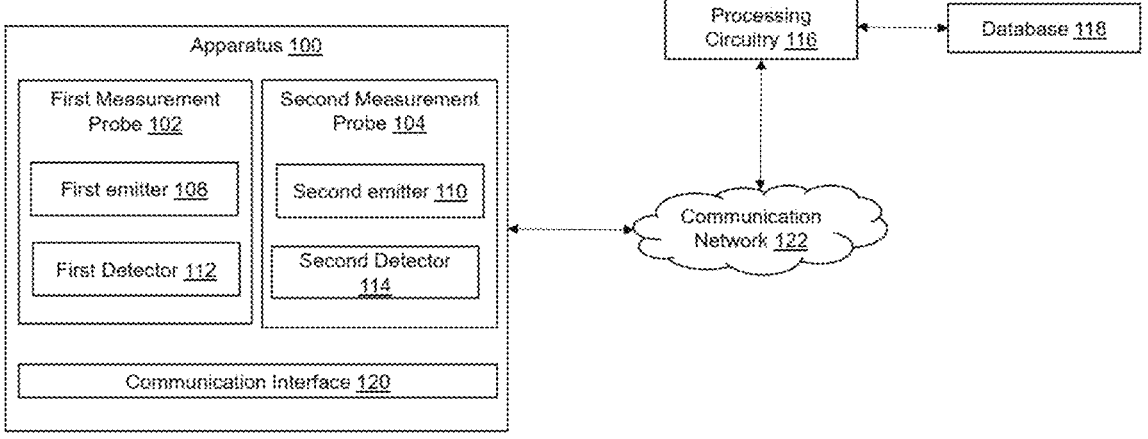
FIG. 1C illustrates another block diagram of the apparatus for measuring oxygen saturation, according to another aspect of the present disclosure.

FIG. 1C illustrates a block diagram of the apparatus 100 for measuring oxygen saturation, according to another aspect of the present disclosure. As illustrated in FIG. 1C that is another embodiment of FIG. 1B, the apparatus 100 may include the first probe 102, the second probe 104, the first emitter 108, the second emitter 110, the first detector 112, the second detector 114, the processing circuitry 116, the database 118, a communication interface 120, and a communication network 122.

The communication interface 120 may be coupled to the communication network 122. The communication network 122 may facilitate data exchange between the first probe 102, the second probe 104 and the processing circuitry 116.

The communication interface 120 may include suitable logic, circuitry, and interfaces that may be configured to establish and enable communication between the first probe 102, the second probe 104, and the communication network 122. The communication interface 120 may be implemented by use of various known technologies to support wired or wireless communication of the apparatus 100 with the communication network 122. The communication interface 120 may include, but may not be limited to, an antenna, a RF transceiver, one or more amplifiers, a tuner, one or more oscillators, a digital signal processor, a CODEC chipset, a SIM card, a local buffer circuit or the like.

In some aspects of the present disclosure, the communication interface 120 may be configured to transmit data from the first probe 102 and the second probe 104 to the processing circuitry 116 via the communication network 122. The data transmitted may include the detected light signals from the first detector 112 and the second detector 114. The communication interface 120 may further be configured to receive instructions or commands from the processing circuitry 116 and relay them to the first probe 102 and the second probe 104.

The communication network 122 may include suitable logic, circuitry, and interfaces that may be configured to provide a plurality of network ports and a plurality of communication channels for transmission and reception of data related to operations of various entities in the apparatus 100. Each network port may correspond to a virtual address (or a physical machine address) for transmission and reception of the communication data. For example, the virtual address may be an Internet Protocol Version 4 (IPV4) (or an IPV6 address) and the physical address may be a Media Access Control (MAC) address.

The communication network 122 may be associated with an application layer for implementation of communication protocols based on one or more communication requests from the first probe 102, the second probe 104, and the processing circuitry 116. The communication data may be transmitted or received, via the communication protocols. Examples of the communication protocols may include, but may not be limited to, Hypertext Transfer Protocol (HTTP), File Transfer Protocol (FTP), Simple Mail Transfer Protocol (SMTP), Domain Network System (DNS) protocol, Common Management Interface Protocol (CMIP), Transmission Control Protocol and Internet Protocol (TCP/IP), User Datagram Protocol (UDP), Long Term Evolution (LTE) communication protocols, or any combination thereof.

In one aspect, the communication data may be transmitted or received via at least one communication channel of a plurality of communication channels in the communication network 122. The communication channels may include, but may not be limited to, a wireless channel, a wired channel, a combination of wireless and wired channel thereof. The wireless or wired channel may be associated with a data standard which may be defined by one of a Local Area Network (LAN), a Personal Area Network (PAN), a Wireless Local Area Network (WLAN), a Wireless Sensor Network (WSN), Wireless Area Network (WAN), Wireless Wide Area Network (WWAN), a Metropolitan Area Network (MAN), a Satellite Network, the Internet, a Fiber Optic Network, a Coaxial Cable Network, an Infrared (IR) network, a Radio Frequency (RF) network, and a combination thereof.

The communication interface 120 and the communication network 122 may work in conjunction to enable real-time data transmission between the first probe 102, the second probe 104, and the processing circuitry 116. This real-time data transmission may allow for continuous monitoring of oxygen saturation levels, potentially improving the accuracy and timeliness of measurements.

In some aspects of the present disclosure, the communication interface 120 and the communication network 122 may be configured to support secure data transmission. This may involve the use of encryption protocols to protect sensitive patient data during transmission. The secure transmission capabilities may be particularly important in clinical settings where patient privacy may be a concern.

The communication interface 120 and the communication network 122 may further be configured to support multiple data streams simultaneously. This capability may allow the apparatus 100 to process data from multiple probes or multiple patients concurrently, potentially increasing the efficiency and versatility of the system.

In some aspects of the present disclosure, the communication interface 120 and the communication network 122 may be designed to be compatible with existing medical information systems. This compatibility may allow for seamless integration of the apparatus 100 into existing healthcare infrastructure, potentially facilitating the adoption and use of the system in various clinical settings.

The communication interface 120 and the communication network 122 may also be configured to support remote monitoring capabilities. This feature may allow healthcare providers to monitor oxygen saturation levels from a distance, potentially enabling telemedicine applications and improving patient care in remote or underserved areas.

The communication network 122 may facilitate data exchange between the first probe 102, the second probe 104 and the processing circuitry 116. As illustrated in FIG. 1C, the processing circuitry 116 and the database 118 may not be a part of the apparatus 100 and the processing circuitry 116 may be coupled to the apparatus 100 by way of the communication network 122. Further, the processing circuitry 116 may be connected to the database 118 for storing and retrieving measurement data.

In operation, the processing circuitry 116 may process the detected signals from the first probe 102 and the second probe 104 to determine reflectance and transmittance values. The processing circuitry 116 may then determine and rescale absorbance values, determine coefficients of absorbers, and ultimately determine oxygen saturation values. The results and related data may be stored in and retrieved from the database 118 as needed.

Examples of the processing circuitry 116 may include, but are not limited to, an Application Specific Integrated Circuit (ASIC) processor, a Reduced Instruction Set Computing (RISC) Processor, a Complex Instruction Set Computing (CISC) Processor, a Field Programmable Gate Array (FPGA), and the like. Aspects of the present disclosure are intended to include and/or otherwise cover any type of the processing circuitry 116 including known, related art, and/or later developed technologies.

Although FIG. 1B and FIG. 1C illustrate that the apparatus 100 includes a single processing circuitry 116 and a single database 118, it may be apparent to a person skilled in the art that the scope of the present disclosure may not be limited to it. In various other aspects, the apparatus 100 may include multiple processing circuitries and multiple databases without deviating from the scope of the present disclosure. In such a scenario, each processing circuitry and database may be configured to perform one or more operations in a manner similar to the operations of the processing circuitry 116 and the database 118 as described herein.

As illustrated in FIG. 1C, the communication interface 120 of the apparatus 100 and the communication network 122 may allow for remote processing and data storage. This configuration may facilitate real-time monitoring and data sharing, which could be particularly useful in clinical settings.

In conclusion, the communication interface 120 and the communication network 122 may enable the efficient and secure transmission of data between the probes 102, 104 and the processing circuitry 116, supporting real-time monitoring, multi-patient capabilities, and potential integration with existing healthcare systems. These features may contribute to the overall effectiveness and versatility of the oxygen saturation measurement system.

Figure 2:
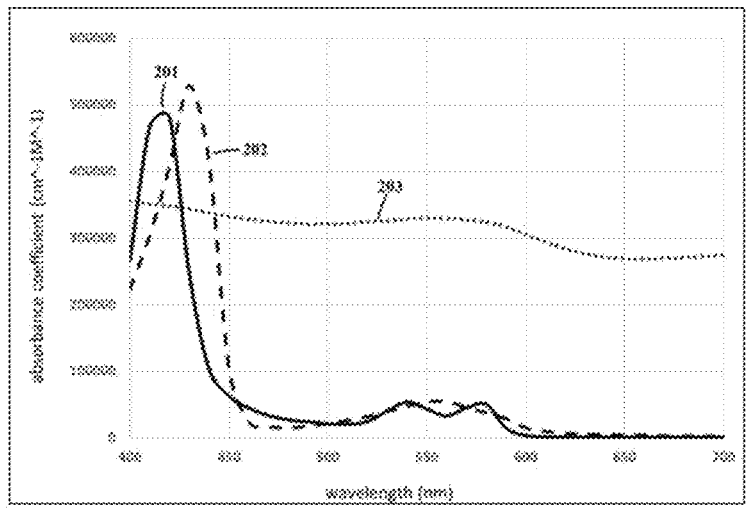
FIG. 2 depicts a graph showing spectral absorbance coefficients versus wavelength for different absorbers, according to another aspect of the present disclosure.

FIG. 2 illustrates a graph that depicts spectral absorbance coefficients versus wavelength for different absorbers. The graph may include an oxyhemoglobin spectral absorbance coefficients 201, a deoxyhemoglobin spectral absorbance coefficients 202, and skin and tissue spectral absorbance coefficients 203. The oxyhemoglobin spectral absorbance coefficients 201 is represented by a solid line with a prominent peak around 450 nm that rapidly decreases and levels off at longer wavelengths. The deoxyhemoglobin spectral absorbance coefficients 202 is represented by a dashed line that follows a similar pattern but with a slightly shifted and broader peak. The skin and tissue spectral absorbance coefficients 203 is represented as a dotted line that maintains a relatively constant value across the wavelength range from 400 nm to 700 nm.

The x-axis of the graph represents the wavelength in nanometers (nm), ranging from 400 nm to 700 nm. The y-axis represents the absorbance coefficient in units of $cm^{-1}M^{-1}$, ranging from 0 to 600,000.

The oxyhemoglobin spectral absorbance coefficients 201 may be represented by a solid line. The solid line may show a sharp peak around 420-450 nm, followed by a rapid decrease and then leveling off at longer wavelengths. The peak may represent the maximum absorption of light by oxyhemoglobin, which occurs in the blue-green region of the visible spectrum.

The deoxyhemoglobin spectral absorbance coefficients 202 may be represented by a dashed line. This line may follow a similar pattern to the oxyhemoglobin curve, but with a slightly shifted and broader peak. The differences in the absorption spectra between oxyhemoglobin and deoxyhemoglobin form the basis for determining oxygen saturation levels.

The skin and tissue spectral absorbance coefficients 203 may be represented by a dotted line. This line may maintain a relatively constant value across the entire wavelength range, with a slight gradual decrease towards higher wavelengths. The relatively constant absorption by skin and tissue across the visible spectrum may contribute to the need for correction in oxygen saturation measurements.

As illustrated in the FIG. 2, the graph may illustrate the distinct absorption patterns of oxyhemoglobin, deoxyhemoglobin, and skin/tissue, and provide a visual representation of the basis for oxygen saturation measurements. This information may be crucial for understanding the principles behind the operation of the apparatus 100 and may aid in the development of more accurate measurement techniques.

As used herein, "spectral absorbance coefficients" refers to the measure of portion of the light signals that may be absorbed by the absorbers at different wavelengths. The units of these coefficients are typically expressed in $cm^{-1}M^{-1}$, which represents the absorbance per unit path length and concentration.

Figure 3:
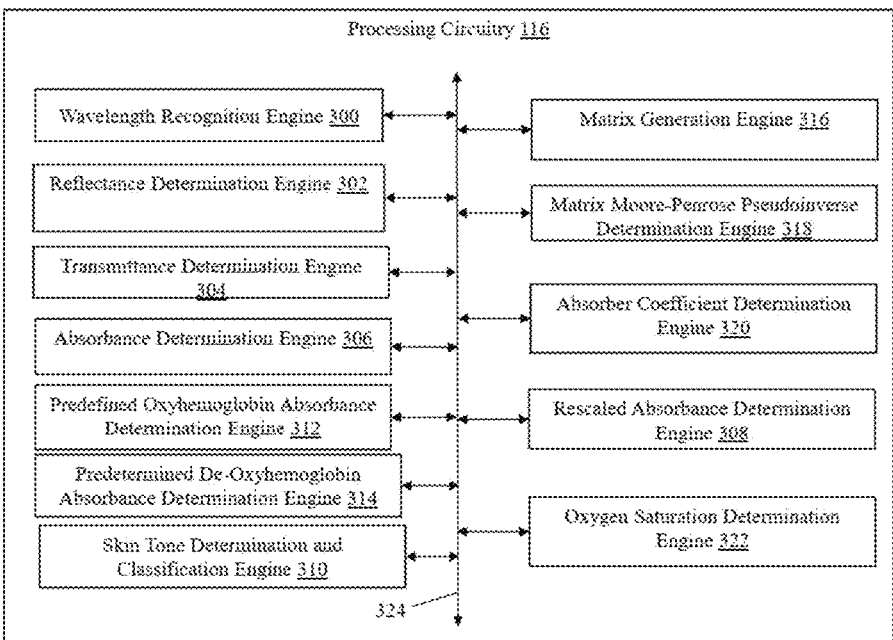
FIG. 3 illustrates a block diagram of processing circuitry for determining oxygen saturation, according to another aspect of the present disclosure.

FIG. 3 illustrates a block diagram of the processing circuitry 116 for determining oxygen saturation with correction for skin and tissue absorption, according to another aspect of the present disclosure. The processing circuitry 116 may include a plurality of engines 300-322 that communicating via the data bus 324. The plurality of engines may include a wavelength recognition engine 300, a reflectance determination engine 302, a transmittance determination engine 304, an absorbance determination engine 306, a rescaled absorbance determination engine 308, a skin tone determination and classification engine 310, a predefined oxyhemoglobin absorbance determination engine 312, a predefined de-oxyhemoglobin absorbance determination engine 314, a matrix generation engine 316, a matrix moore-penrose-pseudoinverse determination engine 318, a absorber coefficient determination engine 320, and an oxygen saturation determination engine 322.

The wavelength recognition engine 300 may be configured to recognize and process the set of wavelengths used in the light signals emitted by the first probe 102 and the second probe 104. In some aspects of the present disclosure, the wavelength recognition engine 300 may be configured to identify wavelengths in an interval of 10 nm within a visible wavelength range of 400 nanometres (nm) to 700 nm by way of the plurality of bandpass filters.

The reflectance determination engine 302 may be configured to determine a set of reflectance values based on the set of light signals detected by one of, the first probe 102, the second probe 104, or a combination thereof. In some aspects of the present disclosure, the reflectance determination engine 302 may be configured to process reflected light signals detected by the first detector 112 and the second detector 114. In some aspects, the set of reflectance values may be determined as percent reflectance for the set of wavelength of the light signals by the body portion 106.

The transmittance determination engine 304 may be configured to determine a set of transmittance values based on the set of light signals detected by one of, the first probe 102, the second probe 104, or a combination thereof. In some aspects of the present disclosure, the transmittance determination engine 304 may be configured to process transmitted light signals detected by the first detector 112 and the second detector 114. In some aspects, the set of transmittance values may be determined as percent transmittance for the set of wavelength of the light signals by the body portion 106.

The absorbance determination engine 306 may be configured to determine first and second set of absorbance values corresponding to the set of reflectance values and the set of transmittance values, respectively. In some aspects of the present disclosure, the absorbance determination engine 306 may be configured to determine the first and second set of absorbance values by way of an equation:

$$absorbance = (100 - reflectancevalue)$$

The rescaled absorbance determination engine 308 may be configured to rescale the first and second set of absorbance values with respect to predefined absorbance values of the first and second absorbers. In some aspects of the present disclosure, the rescaled absorbance determination engine 308 may be configured to rescale the absorbance values by way of an equation:

$$rescaledabsorbance = (100 - reflectancevalue)/0.00025$$

The skin tone determination and classification engine 310 may be configured to determine and classify a skin tone of the body portion 106 by way of a huvic scale. In some aspects of the present disclosure, the skin tone determination and classification engine 310 may be further configured to adjust the determined first and second set of absorbance values based on the classified skin tone of the body portion 106.

The predefined oxyhemoglobin absorbance determination engine 312 may be configured to determine predefined absorbance values for oxyhemoglobin based on known spectral data, such as that represented by the oxyhemoglobin spectral absorbance coefficients 201.

The predefined de-oxyhemoglobin absorbance determination engine 314 may be configured to determine predefined absorbance values for deoxyhemoglobin based on known spectral data, such as that represented by the deoxyhemoglobin spectral absorbance coefficients 202.

The matrix generation engine 316 may be configured to generate at least one matrix based on the set of wavelengths, the rescaled first set of absorbance values, and the predefined absorbance values of the first and second absorbers. In some aspects, the at least matrix may be a 31×3 matrix A such that the matrix A has three columns having the rescaled first set of absorbance values, and the predefined absorbance values of the first and second absorbers and thirty one rows having the set of wavelengths.

The Matrix Moore-Penrose Pseudoinverse Determination Engine 318 may be configured to determine the Moore-Penrose pseudoinverse of the at least one matrix generated by the Matrix Generation Engine 316. In some aspects, when the at least one matrix may be the matrix A then the Moore-Penrose pseudoinverse of the matrix A is determined by way of the equation: $(A^T A)^{-1} A^T$.

The Absorber Coefficient Determination Engine 320 may be configured to determine first through third coefficients of the first through third absorbers, respectively, by performing matrix multiplication of the Moore-Penrose pseudoinverse of a first matrix to a second matrix formed based on rescaled second set of absorbance values.

In some aspects, the first matrix may be the matrix A and the second matrix may be a 31×1 column matrix b such that the matrix b has one column having the set of transmittance values and the thirty one rows having the set of wavelengths. Further, the first through third coefficients of the first through third absorbers may be a 3×1 matrix X such that the matrix X may have one column having unknown first through third coefficients of the first through third absorbers and the thirty one rows having the set of wavelengths. Furthermore, the first through third coefficients of the first through third absorbers may be determined by way of the equation: $x=(A^T A)^{-1} A^{T}*b$.

The Oxygen Saturation Determination Engine 322 may be configured to determine an oxygen saturation value based on the first and second coefficients such that the oxygen saturation value may be corrected for skin and tissue absorption. In some aspects of the present disclosure, the Oxygen Saturation Determination Engine 322 may be configured to determine the oxygen saturation value by way of the equation:

$$\text{oxygenSaturation} =$$
$$(100 * \text{firstcoefficient})/(\text{firstcoefficient} + \text{secondcoefficient})$$

The data bus 324 may be configured to facilitate communication and data exchange between the engines 300-322 within the processing circuitry 116.

In operation, the processing circuitry 116 may receive input data from the first probe 102 and the second probe 104 through the communication interface 120 and the communication network 122. The Wavelength Recognition Engine 300 may process the wavelength information of the received light signals. The Reflectance Determination Engine 302 and the Transmittance Determination Engine 304 may then determine the reflectance and transmittance values, respectively. These values may be passed to the Absorbance Determination Engine 306, which may calculate a first and second absorbance values corresponding to the reflectance and transmittance values, respectively. The Rescaled Absorbance Determination Engine 308 may rescale the first and second absorbance values. Further, the Skin Tone Determination and Classification Engine 310 may adjust the rescaled first and second absorbance values based on skin tone information by detecting the skin tone of the user and classifying the skin tone of the user using the Huvic scale. The Matrix Generation Engine 316 may create the at least one matrix using the adjusted rescaled absorbance values along with predefined absorbance data from the Predefined Oxyhemoglobin Absorbance Determination Engine 312 and the Predetermined De-Oxyhemoglobin Absorbance Determination Engine 314. The Matrix Moore-Penrose Pseudo-inverse Determination Engine 318 and the Absorber Coefficient Determination Engine 320 may then perform the necessary matrix operations to determine the coefficients of the absorbers. Finally, the Oxygen Saturation Determination Engine 322 may use these coefficients to calculate the oxygen saturation value, which may be corrected for skin and tissue absorption.

The inclusion of skin tone classification and correction may improve the accuracy of measurements across diverse skin types. Furthermore, the use of matrix operations and the Moore-Penrose pseudoinverse may allow for robust handling of measurement data, potentially improving the reliability of the oxygen saturation determination.

As used herein, "Moore-Penrose pseudoinverse" refers to a generalization of the inverse matrix that can be applied to non-square matrices or singular square matrices. The Moore-Penrose pseudoinverse may be particularly useful in solving systems of linear equations where a unique solution may not exist.

As used herein, "huvic scale" refers to a standardized scale for classifying human skin color. The huvic scale may provide a more uniform and comprehensive representation of skin tones compared to other existing scales, potentially improving the accuracy of skin tone-based corrections in oxygen saturation measurements.

Figure 4:
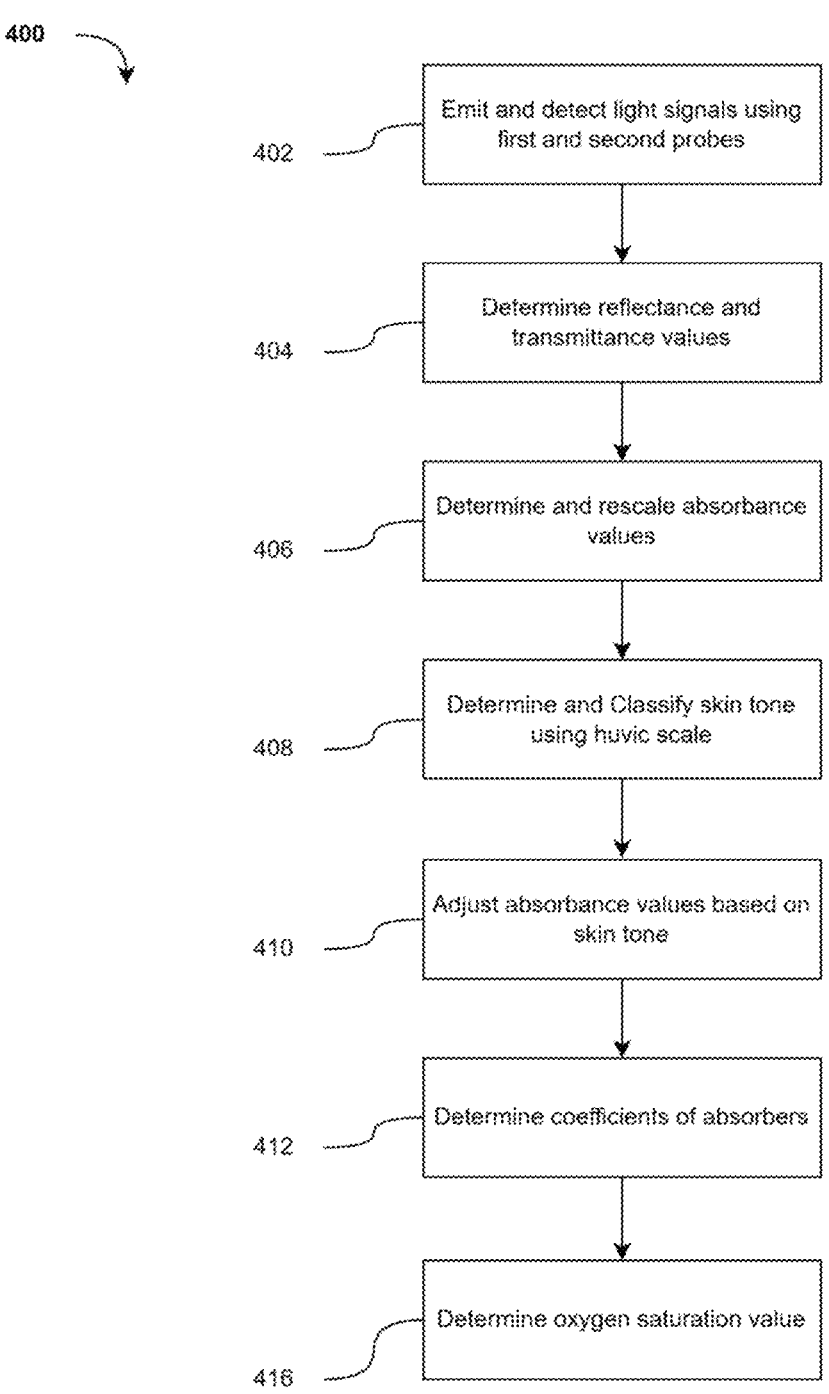
FIG. 4 illustrates a flowchart of a method for determining oxygen saturation with skin tone correction, according to another aspect of the present disclosure.

FIG. 4 illustrates a flowchart of a method 400 for determining oxygen saturation with skin tone correction. The method 400 begins with step 402, where light signals are emitted and detected using first and second probes. In step 404, reflectance and transmittance values are determined from the detected light signals. The method 400 proceeds to step 406, where absorbance values are determined and rescaled based on the reflectance and transmittance values. Step 408 follows, involving the determination and classification of skin tone using a huvic scale. In step 410, the absorbance values are adjusted based on the classified skin tone. The method 400 then moves to step 412, where coefficients of absorbers are determined from the adjusted absorbance values. The method 400 concludes with step 416, where an oxygen saturation value is determined using the coefficients of absorbers. The steps are connected by directional arrows indicating the sequential flow of the process from top to bottom.

At step 402, the apparatus may emit light signals using the first probe and the second probe. The first probe and the second probe may be configured to emit light signals at specific wavelengths, typically in the visible spectrum range of 400 nm to 700 nm. The emitted light signals may interact with the body portion, and the resulting reflected and transmitted light signals may be detected by the first detector and the second detector.

At step 404, the apparatus may determine reflectance and transmittance values from the detected light signals. The Reflectance Determination Engine may process the reflected light signals to determine the reflectance values, while the Transmittance Determination Engine may process the transmitted light signals to determine the transmittance values. These values may be determined for each wavelength in the set of emitted light signals.

At step 406, the apparatus may determine and rescale absorbance values based on the reflectance and transmittance values. The Absorbance Determination Engine may calculate the absorbance values using an equation. The Rescaled Absorbance Determination Engine may then rescale these absorbance values using another equation.

At step 408, the apparatus may determine and classify the skin tone of the body portion using a huvic scale. The Skin Tone Determination and Classification Engine may analyze the reflected light signals to determine the skin tone and classify it according to the huvic scale. This scale may provide a more comprehensive and accurate representation of skin tone compared to other existing scales.

At step 410, the apparatus may adjust the absorbance values based on the classified skin tone. The Rescaled Absorbance Determination Engine may apply corrections to the absorbance values based on the skin tone classification. This adjustment may help to account for variations in light absorption due to different skin pigmentations.

At step 412, the apparatus may determine coefficients of absorbers from the adjusted absorbance values. The Absorber Coefficient Determination Engine may use matrix operations, including the Moore-Penrose pseudoinverse, to calculate the coefficients of the first through third absorbers (oxyhemoglobin, deoxyhemoglobin, and skin/tissue).

At step 416, the apparatus may determine an oxygen saturation value using the coefficients of absorbers. The Oxygen Saturation Determination Engine may calculate the oxygen saturation value using an equation. This calculation may provide an oxygen saturation value that is corrected for skin and tissue absorption.

In operation, the method 400 may provide a comprehensive approach to determining oxygen saturation while accounting for variations in skin tone. By incorporating skin tone classification and correction, the method may offer improved accuracy across a diverse range of skin types. The use of rescaled absorbance values and matrix operations may allow for more precise calculations, potentially leading to more reliable oxygen saturation measurements.

The method 400 may offer several advantages. The step-by-step approach allows for systematic processing of the measurement data, potentially reducing errors and improving overall accuracy. The inclusion of skin tone classification and correction may make the method more versatile and applicable across diverse populations. Furthermore, the use of advanced mathematical techniques, such as the Moore-Penrose pseudoinverse, may enable the method to handle complex data relationships more effectively.

Examples of the huvic scale used in step 408 may include, but are not limited to, a 100-point scale ranging from very light (Huvic 0) to very dark (Huvic 100) skin tones. The huvic scale may be designed to provide more granular and objective skin tone classification compared to existing scales. Aspects of the present disclosure are intended to include and/or otherwise cover any type of skin tone classification scale known to a person having ordinary skill in the art, without deviating from the scope of the present disclosure.

As used herein, "huvic scale" refers to a standardized scale for classifying human skin color. The huvic scale provides a more uniform and comprehensive representation of skin tones compared to other existing scales, potentially improving the accuracy of skin tone-based corrections in oxygen saturation measurements.

The huvic scale may be designed to address limitations in existing skin tone classification systems, such as the Monk scale. While the Monk scale consists of 10 shades ranging from very light (Monk1) to very dark (Monk10), the huvic scale expands this to a 100-point system. This increased granularity may allow for more precise skin tone classification and, consequently, more accurate corrections in oxygen saturation measurements.

The huvic scale may be defined using both RGB and CIELAB color values. For example, Huvic 0 may correspond to RGB values of (236, 228, 220) and CIELAB values of (91.03, 1.45, 6.88), while Huvic 100 may correspond to RGB values of (29, 12, 7) and CIELAB values of (4.98, 5.96, 4.38). The intermediate values may be calculated to provide a smooth gradient between these extremes.

In some aspects of the present disclosure, the Skin Tone Determination and Classification Engine may be configured to use the huvic scale to classify the skin tone of the body portion being measured. This classification may then be used to apply appropriate corrections to the absorbance values, potentially improving the accuracy of the oxygen saturation determination across a wide range of skin tones.

The use of the huvic scale in the method 400 may offer several advantages. It may provide a more standardized and objective method for skin tone classification compared to subjective visual assessments. The increased granularity of the scale may allow for more precise corrections in oxygen saturation measurements. Furthermore, compatibility of the huvic scale to be used with both RGB and CIELAB color values may make the scale more versatile and applicable across different imaging and measurement systems.

In some aspects of the present disclosure, the method 400 may be implemented in various medical devices and systems beyond the specific apparatus described earlier. For example, the method may be incorporated into portable oxygen saturation monitors, hospital bedside monitors, or even wearable health tracking devices. The versatility of the method, particularly its ability to account for skin tone variations, may make it valuable in diverse healthcare settings and for a wide range of patient populations.

The method 400 may further be extended to include additional steps or refinements. For instance, it may incorporate temperature compensation to account for variations in skin temperature that could affect light absorption. It may also include steps to account for motion artifacts or other sources of measurement noise, further improving the accuracy and reliability of the oxygen saturation determination.

In some aspects of the present disclosure, the method 400 may be implemented in software, allowing for easy updates and improvements as new research and data become available. This software implementation may enable the method to be easily integrated into existing medical devices through firmware updates, potentially extending the lifespan and improving the performance of current oxygen saturation measurement equipment.

The method 400 may further be adapted to provide continuous monitoring of oxygen saturation over time. In such implementations, the method may include additional steps for trend analysis and alert generation when oxygen saturation levels fall outside of predetermined safe ranges. This capability may be particularly valuable in critical care settings where continuous monitoring of patient oxygenation is crucial.

In conclusion, the apparatus 100 and the method 400 for determining oxygen saturation with skin tone correction represents a significant advancement in the field of medical diagnostics. By incorporating sophisticated skin tone classification and correction techniques, along with advanced mathematical processing, the method may offer improved accuracy and reliability in oxygen saturation measurements across diverse patient populations. Its potential for implementation in a wide range of medical devices and systems may make it a valuable tool in various healthcare settings, from routine check-ups to critical care monitoring.

Thus, the Apparatus and Method Provide Several Significant Technical Advantages:

1) The incorporation of sophisticated skin tone classification using the huvic scale enables more accurate oxygen saturation measurements across diverse patient populations.

2) The dual-probe configuration allows for simultaneous reflectance and transmittance measurements, improving measurement precision.

3) Advanced signal processing techniques, including the use of Moore-Penrose pseudoinverse in matrix operations, enhance the system's ability to handle complex data relationships.

4) The incorporation of machine learning algorithms enables the device to adapt and improve its accuracy over time by learning from large datasets.

5) The modular design of the apparatus facilitates easy upgrades and integration of new technologies, extending its lifespan and versatility.

6) The system's ability to perform continuous monitoring with trend analysis and alert generation significantly enhances its clinical utility, particularly in critical care settings.

The invention claimed is:

1. An apparatus comprising:
first and second probes adapted to be disposed on a body portion having first through third absorbers, and configured to emit and detect a set of light signals corresponding to a set of wavelengths, wherein the first absorber, the second absorber, and the third absorber is oxyhaemoglobins, deoxyhaemoglobins, and skin/tissues, respectively;
processing circuitry that is coupled to the first and second probes, and configured to:
determine a set of reflectance values and a set of transmittance values based on the set of light signals detected by one of, the first probe, the second probes, or a combination thereof;
determine and rescale, first and second set of absorbance values corresponding to the set of reflectance values and the set of transmittance values, respectively, wherein each absorbance value of the first and second set of absorbance values are rescaled with respect to predefined absorbance values of the first and second absorbers;
determine first through third coefficients of the first through third absorbers, respectively, based on the rescaled first and second set of absorbance values; and
determine an oxygen saturation value based on the first and second coefficients such that the oxygen saturation value is corrected for skin and tissue absorption.

2. The apparatus of claim 1, wherein the processing circuitry is configured to control one of, the first probe or the second probe, to emit the set of light signals in an interval of 10 nm within a visible wavelength range of 400 nanometres (nm) to 700 nm.

3. The apparatus of claim 1, wherein the first probe comprising: (i) a first emitter and (ii) a first detector; and the second probe comprising: (i) a second emitter and (ii) a second detector;
wherein the first and second emitter is configured to emit a first and second set of light signals to illuminate a first and second side of the body portion, respectively;
the first detector is configured to detect a set of reflected signals of the first set of light signals and to detect a set of transmitted signals of the second set of light signals; and
the second detector is configured to detect a second set of reflected signals of the second set of light signals and to detect a set of transmitted signals of the first set of light signals.

4. The apparatus of claim 1, wherein the processing circuitry is configured to determine and rescale the first and second set of absorbance values by way of an equation:

$$\text{rescaled absorbance}=(100-\text{reflectance value})/0.00025.$$

5. The apparatus of claim 1, wherein the processing circuitry is configured to determine the first through third coefficients of the first through third absorbers, respectively, by performing matrix multiplication of Moore-Penrose pseudoinverse of a first matrix formed that is based on the set of wavelengths, the rescaled first set of absorbance values, and the predefined absorbance values of the first and second absorbers, to a second matrix formed that is based on rescaled second set of absorbance values.

6. The apparatus of claim 1, wherein the processing circuitry is configured to determine the oxygen saturation value by way of an equation:

$$\text{oxygenSaturation} =$$

$$(100 * \text{firstcoefficient})/(\text{firstcoefficient} + \text{secondcoefficient}).$$

7. The apparatus of claim 1, wherein the processing circuitry is configured to:
determine the first and second set of absorbance values corresponding to the set of reflectance values and the set of transmittance values by way of an equation:

$$\text{absorbance} = (100 - \text{reflectance value});$$

and
rescale the determined first and second set of absorbance values by way of an equation:

$$\text{rescaled absorbance} = \text{absorbance}/0.00025.$$

8. The apparatus of claim 1, the processing circuitry is configured to:
determine and classify a skin tone of the body portion by way of a huvic scale;
adjust the determined first and second set of absorbance values based on the classified skin tone of the body portion.

9. A method comprising:
emitting and detecting, by way of first and second probes disposed on a body portion having first through third absorbers, a set of light signals corresponding to a set of wavelengths, wherein the first absorber, the second absorber, and the third absorber is oxyhaemoglobins, deoxyhaemoglobins, and skin/tissues, respectively;
determining, by way of processing circuitry coupled to the first and second probes, a set of reflectance values and a set of transmittance values based on the set of light signals detected by one of, the first probe, the second probe, or a combination thereof;
determining and rescaling, by way of the processing circuitry, first and second set of absorbance values corresponding to the set of reflectance values and the set of transmittance values, respectively, wherein each absorbance value of the first and second set of absorbance values are rescaled with respect to predefined absorbance values of the first and second absorbers;
determining, by way of the processing circuitry, first through third coefficients of the first through third absorbers, respectively, based on the rescaled first and second set of absorbance values; and determining, by way of the processing circuitry, an oxygen saturation value based on the first and second coefficients such that the oxygen saturation value is corrected for skin and tissue absorption.

10. The method of claim 9, further comprising:

controlling, by way of the processing circuitry, one of, the first probe or the second probe, to emit the set of light signals in an interval of 10 nm within a visible wavelength range of 400 nanometres (nm) to 700 nm.

11. The method of claim 9, wherein:

the first probe comprises: (i) a first emitter and (ii) a first detector; and the second probe comprises: (i) a second emitter and (ii) a second detector;

the method further comprising:

emitting, by way of the first and second emitter, a first and second set of light signals to illuminate a first and second side of the body portion, respectively;

detecting, by way of the first detector, a set of reflected signals of the first set of light signals and a set of transmitted signals of the second set of light signals; and detecting, by way of the second detector, a second set of reflected signals of the second set of light signals and a set of transmitted signals of the first set of light signals.

12. The method of claim 9, wherein determining and rescaling the first and second set of absorbance values comprises:

applying an equation: rescaled absorbance=(100−reflectance value)/0.00025.

13. The method of claim 9, wherein determining the first through third coefficients of the first through third absorbers, respectively, comprises:

performing matrix multiplication of Moore-Penrose pseudoinverse of a first matrix formed that is based on the set of wavelengths, the rescaled first set of absorbance values and the predefined absorbance values of the first and second absorbers, to a second matrix formed that is based on rescaled second set of absorbance values.

14. The method of claim 9, wherein determining the oxygen saturation value comprises:

applying an equation: oxygen Saturation=(100*first coefficient)/(first coefficient+second coefficient).

15. The method of claim 9, further comprising:

determining the first and second set of absorbance values corresponding to the set of reflectance values and the set of transmittance values by applying an equation:

absorbance=(100−reflectance value); and rescaling the determined first and second set of absorbance values by applying an equation:

rescaled absorbance=absorbance/0.00025.

16. The method of claim 9, further comprising:

determining and classifying, by way of the processing circuitry, a skin tone of the body portion using a huvic scale;

adjusting the determined first and second set of absorbance values based on the classified skin tone of the body portion.

* * * * *